(12) United States Patent
Isawa et al.

(10) Patent No.: US 7,208,520 B2
(45) Date of Patent: Apr. 24, 2007

(54) CRYSTALS OF HYDROXYNOREPHEDRINE DERIVATIVE

(75) Inventors: Hidetoshi Isawa, Fukui (JP); Yukihiko Hotei, Nagano (JP); Kiyoshi Kasai, Fukui (JP); Junichi Sonehara, Fukui (JP); Satoshi Akahane, Nagano (JP); Hiromu Harada, Nagano (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 75 days.

(21) Appl. No.: 10/489,343

(22) PCT Filed: Aug. 27, 2002

(86) PCT No.: PCT/JP02/08596

§ 371 (c)(1),
(2), (4) Date: Mar. 12, 2004

(87) PCT Pub. No.: WO03/024916

PCT Pub. Date: Mar. 27, 2003

(65) Prior Publication Data
US 2004/0242686 A1    Dec. 2, 2004

(30) Foreign Application Priority Data
Sep. 13, 2001    (JP) ............................. 2001-277345

(51) Int. Cl.
*A01N 37/12*    (2006.01)
*A01N 37/44*    (2006.01)
*A61K 31/24*    (2006.01)

(52) U.S. Cl. ............ 514/539; 514/532; 514/540; 514/567; 514/568; 514/617; 560/37; 560/42; 562/451; 564/165

(58) Field of Classification Search ................ 514/539, 514/532, 540, 567, 568, 617; 560/37, 42; 562/451; 564/165
See application file for complete search history.

(56) References Cited

U.S. PATENT DOCUMENTS 6,538,152 B1 *  3/2003  Tanaka et al. ................. 560/42

FOREIGN PATENT DOCUMENTS

| EP | 1095932 A1 | 5/2001 |
|---|---|---|
| JP | 2000-212137 A2 | 8/2000 |
| JP | 2000-212138 A2 | 8/2000 |
| JP | 2000-212139 A2 | 8/2000 |
| WO | WO 00/02846 A1 | 1/2000 |
| WO | WO 00/02846 | * 2/2000 |

* cited by examiner

*Primary Examiner*—Thurman Page
*Assistant Examiner*—Chukwuma Nwaonicha
(74) *Attorney, Agent, or Firm*—Sughrue Mion, PLLC

(57) ABSTRACT

The present invention provides ethyl (−)-2-[4-[2-[[(1S,2R)-2-hydroxy-2-(4-hydroxyphenyl)-1-methylethyl]amino]ethyl]-2,5-dimethylphenoxy]acetate hydrochloride, crystalline forms thereof and pharmaceutical compositions containing them, which have excellent $\beta_3$-adrenoceptor stimulating effects, therapeutic effects on pollakiuria or urinary incontinence and storage stabilities and are useful as a medicament.

10 Claims, 2 Drawing Sheets

CRYSTALS OF HYDROXYNOREPHEDRINE DERIVATIVE

TECHNICAL FIELD

The present invention relates to ethyl (−)-2-[4-[2-[[(1S,2R)-2-hydroxy-2-(4-hydroxyphenyl)-1-methylethyl]amino]ethyl]-2,5-dimethylphenoxy]acetate hydrochloride and in particular crystalline forms thereof, which have $\beta_3$-adrenoceptor stimulating effects and are useful as a medicament for the treatment of pollakiuria or urinary incontinence.

BACKGROUND ART

Ethyl (−)-2-[4-[2-[[(1S,2R)-2-hydroxy-2-(4-hydroxyphenyl)-1-methylethyl ]amino]ethyl]-2,5-dimethylphenoxy]acetate represented by formula (II):

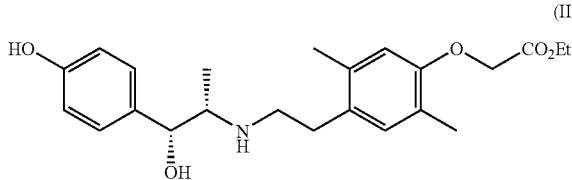

has been disclosed in WO00/02846 by the present applicant and is itself a known compound. This compound has been known to have an excellent $\beta_3$-adrenoceptor stimulating effect and is useful as a medicament for the treatment of pollakiuria or urinary incontinence.

Compound (II) exhibits excellent therapeutic activities for the treatment of pollakiuria or urinary incontinence, while it could have been produced only in amorphous forms by the preparation method as described in WO00/02846. For producing the amorphous compound (II) in a substantially pure form, troublesome purification steps have been required. Compound (II) is difficult to formulate into solid form preparations due to its viscous physical property. Moreover, compound (II) has unsatisfactory stability, and when stored under ordinary conditions for a long period, it has serious problems to discolor and decrease the content of the active ingredient. Accordingly, there is a need for a novel form of compound (II) which has satisfactory storage stability and is usable as a drug substance.

DISCLOSURE OF THE INVENTION

The present inventors had intensively investigated various acid addition salts of compound (II), and found unexpectedly that a hydrochloride salt of compound (II), that is ethyl (−)-2-[4-[2-[[(1S,2R)-2-hydroxy-2-(4-hydroxyphenyl)-1-methyethyl ]amino]ethyl]-2,5-dimethyl-phenoxy]acetate hydrochloride represented by formula (I):

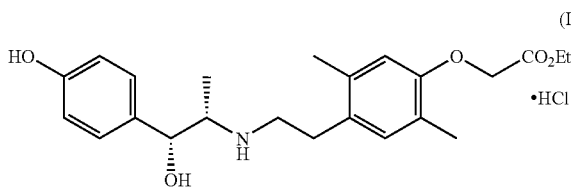

can be obtained in the form of highly crystalline solid. Moreover, the present inventors had investigated crystals of compound (I), and found that crystals of the present invention have surprisingly excellent storage stabilities and are useful for a drug substance. Based on these findings, the present invention has been accomplished.

The present invention therefore provides:
(1) a compound represented by formula (I):

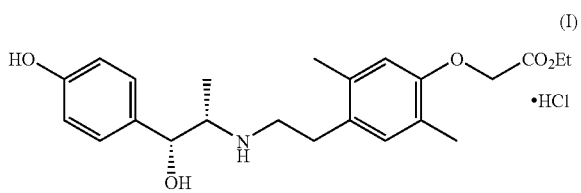

(2) a crystal of a compound according to the above (1);
(3) the crystal according to the above (2) which shows an X-ray powder diffraction pattern having characteristic peaks at a diffraction angle (2θ±0.1 degree) of 8.9, 10.2, 12.9, 14.2, 15.6, 18.4 and 20.6 degrees (hereinafter, referred to as "crystalline form A");
(4) the crystal according to the above (2) which shows an X-ray powder diffraction pattern having characteristic peaks at a diffraction angle (2θ±0.1 degree) of 7.3, 10.1, 12.2, 14.6, 15.9, 16.0, 18.7 and 21.8 degrees (hereinafter, referred to as "crystalline form B");
(5) a pharmaceutical composition which comprises, as an active ingredient, a compound according to any one of the above (1) to (4);
(6) the pharmaceutical composition according to the above (5), for the treatment of pollakiuria or urinary incontinence;
(7) a medicament for treating pollakiuria or urinary incontinence, which comprises, as an active ingredient, a compound according to any one of the above (1) to (4);
(8) a use of a compound according to any one of the above (1) to (4), for the manufacture of a medicament for treating pollakiuria or urinary incontinence; and
(9) a method for treating pollakiuria or urinary incontinence, which comprises administering a therapeutically effective amount of a compound according to any one of the above (1) to (4).

BEST MODE FOR CARRYING OUT THE INVENTION

A compound represented by formula (I) of the present invention, and the particular crystalline forms A and B thereof can be produced as follows.

Compound (II), which is used as the starting material of the present invention, can be prepared in amorphous forms by the known procedure as described in WO00/02846.

Compound (I) can be obtained in crystalline forms by reacting a solution of compound (II) in an appropriate organic solvent, with hydrochloric acid or hydrogen chloride.

Examples of the organic solvent employed in the above reaction include ethanol, carboxylic acid esters such as ethyl acetate and the like, hydrocarbons such as toluene and the like, acetonitrile and the like. The organic solvents can be used either singly or as a mixture of two or more solvents.

The source of HCl can be used in the form of hydrochloric acid, or a solution of the above organic solvent into which gaseous hydrogen chloride is blown.

The reaction of compound (II) with hydrochloric acid or hydrogen chloride takes place immediately. The time required for crystallization varies depending upon crystallization conditions such as the amounts of organic solvents and HCl employed, as well as the crystallization temperature and the like, and it takes ordinarily about 1 to 24 hours. Preferably, the crystallization is carried out by stirring the reaction mixture at a temperature of about 0 to about 30° C. for 1 to 6 hours to provide compound (I).

Recrystallization of compound (I) thus obtained, from a suitable solvent provides crystalline forms A and B, which are the particular crystalline forms of compound (I) of the present invention.

For example, crystalline form A can be obtained as follows. Compound (I) is dissolved in ethanol under heating, and to the resulting solution is added, if necessary, t-butyl methyl ether, isopropanol or water at a temperature of about 40 to about 50° C. with stirring, then the mixture is stirred at a temperature of about 40 to about 50° C. for 1 to 6 hours. Thereafter, the mixture is stirred at a temperature of about 0 to about 30° C. for another 1 to 6 hours to provide crystalline form A.

Crystalline form B can be obtained as follows. Compound (I) is dissolved in ethanol and tetrahydrofuran under heating, and to the resulting mixture is added additional tetrahydrofuran at about 40° C. with stirring. The mixture is stirred at a temperature of about 0 to about 10° C. for 1 to 12 hours to provide crystalline form B.

Figure 1:
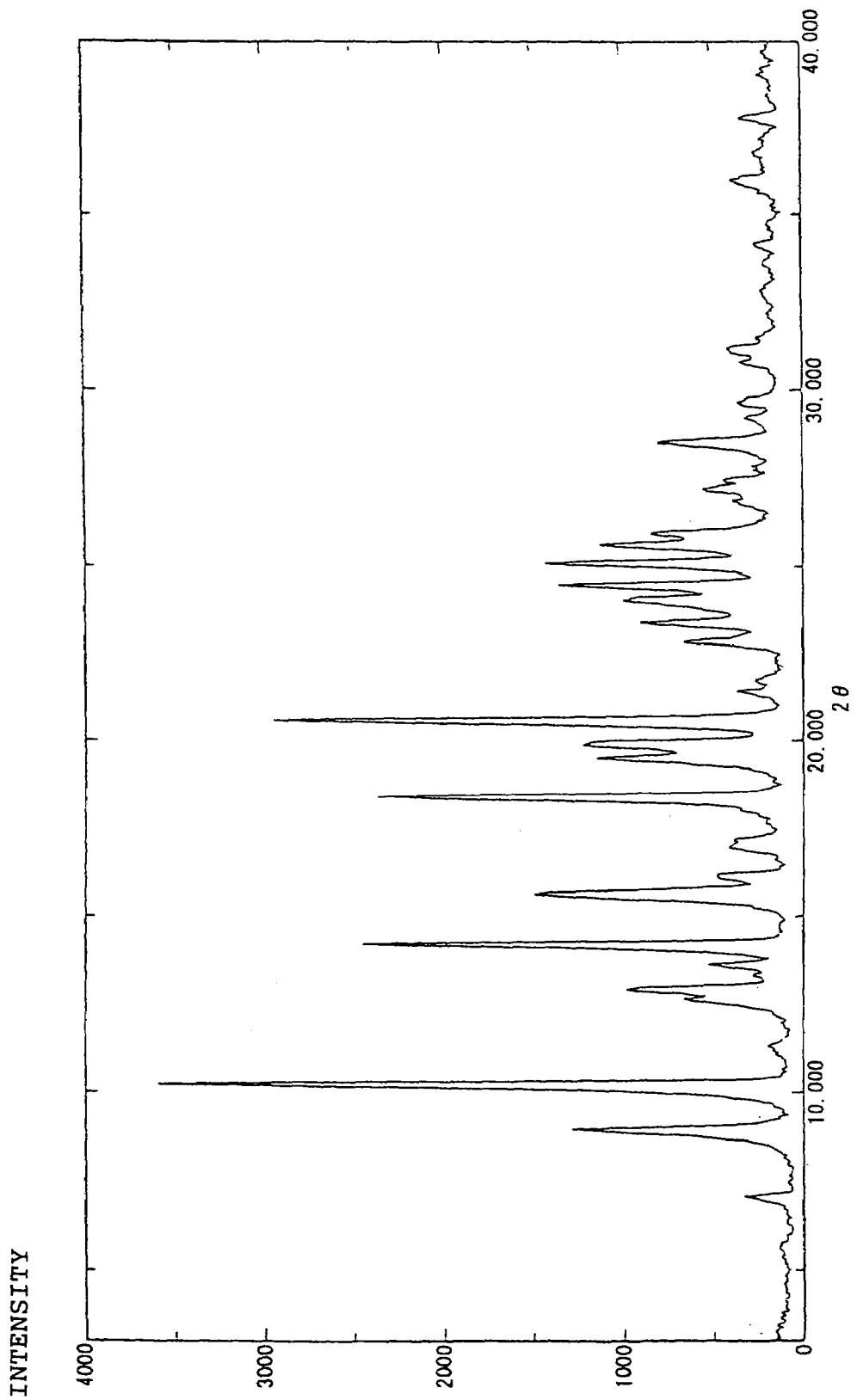
FIG. 1 is an X-ray powder diffraction pattern of crystalline form A of compound (I) obtained in Example 2 where the ordinate shows the X-ray intensity in cps and the abscissa shows the diffraction angle in 2θ.
Figure 2:
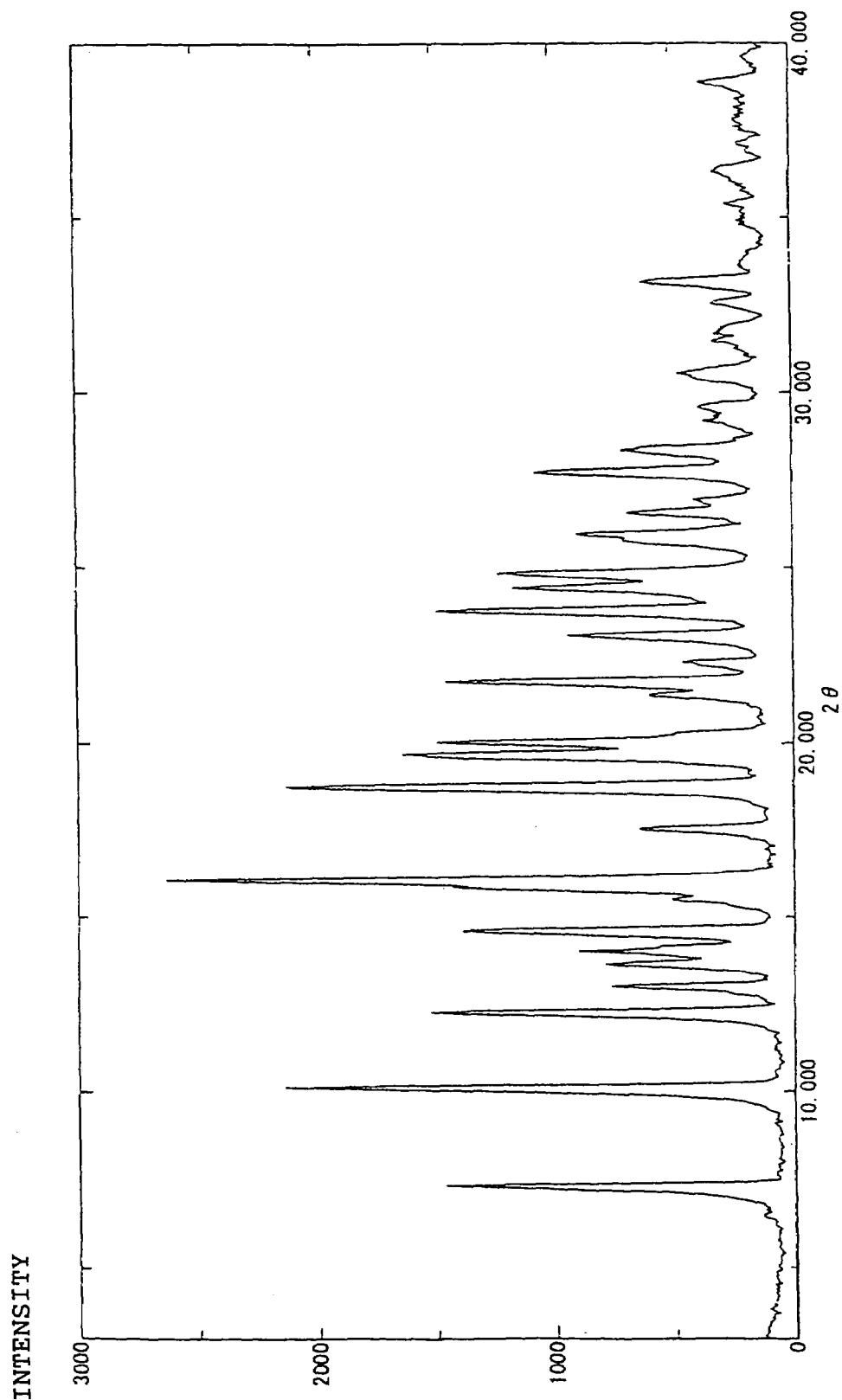
FIG. 2 is an X-ray powder diffraction pattern of crystalline form B of compound (I) obtained in Example 3 where the ordinate shows the X-ray intensity in cps and the abscissa shows the diffraction angle in 2θ.

The crystalline forms A and B of compound (I) thus obtained can be identified by their characteristic diffraction peaks as shown in the X-ray powder diffraction charts of FIGS. 1 and 2:

(1) crystalline form A has characteristic peaks at a diffraction angle (2θ±0.1 degree) of 8.9, 10.2, 12.9, 14.2, 15.6, 18.4 and 20.6 degrees as shown in FIG. 1; and (2) crystalline form B has characteristic peaks at a diffraction angle (2θ±0.1 degree) of 7.3, 10.1, 12.2, 14.6, 15.9, 16.0, 18.7 and 21.8 degrees as shown in FIG. 2.

The crystalline forms A and B of compound (I) can be stored at ordinarily storage conditions such as 25° C., 60% relative humidity and the like for a long period without changing their crystalline forms, and are also chemically stable. The crystalline forms A and B have excellent flowabilities and good handling properties, and are suitable for formulation.

The compound represented by formula (I) of the present invention exhibits an excellent $\beta_3$-adrenoceptor stimulating effect and relaxes bladder detrusor muscle as well as increases the volume of bladder. Therefore, compound (I) of the present invention can be used for the treatment of dysuria such as pollakiuria, urinary incontinence in the case of nervous pollakiuria, neurogenic bladder dysfunction, nocturia, unstable bladder, cystospasm, chronic or acute cystitis, chronic or acute prostatitis, prostatic hypertrophy and the like, idiopathic pollakiuria, idiopathic urinary incontinence and the like.

The compound represented by formula (I) of the present invention can be used, if required, in combination with another medicament for the treatment of dysuria. Examples of such a medicament include anticholinergic agents such as oxybutynin hydrochloride, propiverine hydrochloride, tolterodine, darifenacin, fesoterodine, trospium chloride, KRP-197, YM-905 and the like; smooth muscle relaxants such as flavoxate hydrochloride and the like; $\beta_2$-adrenoceptor agonists such as clenbuterol hydrochloride, formoterol fumarate and the like; $\alpha_1$-adrenoceptor agonists such as midodrine hydrochloride, R-450, GW-515524, ABT-866 and the like; estrogen preparations such as conjugated estrogen, estriol, estradiol and the like; central nervous system agents such as antiepileptic agents, antidepressants and the like such as imipramine, reserpine, diazepam, carbamazepine and the like; neurokinin receptor antagonists such as TAK-637, SB-223956, AZD-5106 and the like; potassium channel openers such as KW-7158, AZD-0947, NS-8, ABT-598, WAY-151616 and the like; vanilloid receptor agonists such as capsaicin, resiniferatoxin and the like; vasopressin 2 receptor agonists such as desmopressin, OPC-51803, WAY-141608 and the like; $\alpha_1$-adrenoceptor antagonists such as tamsulosin, urapidil, naftopidil, silodsin, terazosin, prazosin, alfuzosin, fiduxosin, AIO-8507L and the like; GABA receptor agonists such as baclofen and the like; serotonin receptor antagonists such as REC-15-3079 and the like; dopamine receptor agonists such as L-dopa and the like, or dopamine receptor antagonists; antiallergic agents such as histamine receptor antagonists such as sulplatast tosilate, norastemizole and the like; NO synthase inhibitors such as nitroflurbiprofen and the like.

In the case of using a pharmaceutical composition comprising the compound represented by formula (I) or the crystalline forms thereof for a medical treatment, various dosage forms can be administered depending upon their usages. Exemplary dosage forms include powders, granules, fine granules, dry syrups, tablets, capsules, injections, liquids, ointments, suppositories, poultices and the like, which are administered orally or parenterally.

Pharmaceutical compositions can be formulated by admixing, diluting or dissolving with appropriate pharmaceutical additives such as excipients, disintegrators, binders, lubricants, diluents, buffers, isotonic agents, preservatives, wetting agents, emulsifying agents, dispersing agents, stabilizing agents, solubilizing agents and the like, according to a conventional formulation procedure depending upon their dosage forms.

In the case of using a pharmaceutical composition of the present invention for a medical treatment, the dosage of the compound represented by formula (I) or the crystalline forms thereof is appropriately determined depending on the age, sex or body weight of the individual patient, the severity of the disease, the condition to be treated and the like. A typical dosage for oral administration is in the range of from about 0.01 mg to about 100 mg per day per adult human. A typical dosage for parenteral administration is in the range of from about 0.0003 mg to about 30 mg per day per adult human. The dosages may be administered in single or divided doses of one to several times daily.

Where the compound represented by formula (I) or the crystalline forms thereof is used in combination with another medicament for the treatment of dysuria, pharmaceutical compositions can be formulated by admixing separately each of active ingredients, or admixing concurrently both of active ingredients, with pharmaceutically acceptable additives such as excipient, disintegrator, binder, lubricant, diluent, buffer, isotonic agent, preservative, wetting agent, emulsifying agent, dispersing agent, stabilizing agent, solubilizing agent and the like, and administered separately or concurrently in an oral or pareteral dosage form. Where separately formulated pharmaceutical compositions are used, the compositions may be mixed together with an appropriate diluent, and administered simultaneously. Alternatively, where separately formulated pharmaceutical compositions are used, the compositions may be administered separately, concurrently or at different intervals.

EXAMPLE

The following examples, reference examples and test examples illustrate the invention in further detail. It is to be understood, however, that they are not to be construed as limiting the scope of the invention in any way.

X-ray powder diffraction patterns of the present crystalline forms were obtained using an X-ray diffraction analyzer, RINT1400 (Rigaku) which was operated at 30 kV/100 mA and using CuKα-ray beam. Melting points were determined using a micro melting point apparatus MP-J3 (Yanagimoto). The starting material, compound (II), was prepared according to the procedure as described in Example 2 in WO00/02846.

Reference Example 1

Ethyl (−)-2-[4-[2-[[(1S,2R)-2-hydroxy-2-(4-hydroxyphenyl)-1-methyethyl]amino]ethyl]-2,5-dimethylphenoxy]acetate (Compound(II))

To a mixture of ethyl 2-[4-(2-bromoethyl)-2,5-dimethylphenoxy]acetate (18.1 g), (1R,2S)-p-hydroxynorephedrine (8.0 g) and N,N-dimethylforamide (45 g) was added diisopropylamine (7.26 g), and the resulting mixture was stirred at 100° C. for 1.5 hours under a nitrogen atmosphere. After cooling to room temperature, ethyl acetate (140 g) and water (60 g) were added to the reaction mixture, and the organic layer was separated. The aqueous layer was extracted with additional ethyl acetate (72 g). The combined organic layers were washed with water and brine successively, dried over sodium sulfate, and filtered. The solvent was removed under reduced pressure to afford a crude product (27.8 g). A 15 g portion of the crude product was purified by column chromatography using 400 g of aminopropylsilicagel (eluent: dichloromethane/ethanol=20/1) to give ethyl (−)-2-[4-[2-[[(1S,2R)-2-hydroxy2-(4-hydroxyphenyl)-1-methyethyl]amino]ethyl]-2,5-dimethylphenoxy]acetate (4.48 g) as a colorless amorphous.

$^1$H-NMR(CDCl$_3$)δppm: 0.98 (3H, d, J=6.1 Hz), 1.33 (3H, t, J=7.0 Hz), 2.18 (3H, s), 2.21 (3H, s), 2.6-3.0 (5H, m), 4.30 (2H, q, J=7.0 Hz), 4.50 (1H, d, J=5.5 Hz), 4.61 (2H, s), 6.42 (1H, s), 6.69 (2H, d, J=8.5 Hz), 6.78 (1H, s), 7.05 (2H, d, J=8.6 Hz)

Example 1

Ethyl (−)-2-[4-[2-[[(1S,2R)-2-hydroxy-2-(4-hydroxyphenyl)-1-methyethyl]amino]ethyl]-2,5-dimethylphenoxy]acetate hydrochloride (Compound(I))

A mixture of ethyl 2-[4-(2-bromoethyl)-2,5-dimethylphenoxy]acetate (23 g), (1R,2S)-p-hydroxynorephedrine (10 g), diisopropylamine (9.1 g) and N,N-dimethylforamide (56 g) was heated at 100° C. for 2 hours under a nitrogen atmosphere. After cooling to room temperature, ethyl acetate (180 g) and water (75 g) were added to the reaction mixture. The organic layer was separated, and the aqueous layer was extracted with additional ethyl acetate (90 g). The combined organic layers were washed with water and brine, dried over sodium sulfate, and filtered. The solvent was removed under reduced pressure, and the residue was dissolved in toluene (38.5 g). To the resultant solution was added dropwise 30 weight percent hydrogen chloride solution in ethanol (6.1 g) under ice cooling, and the resulting mixture was stirred at room temperature for 2 hours for crystallization. The precipitated crystals were collected by filtration, dried at 60° C. for 6 hours in vacuo to give 15 g of compound (I). $^1$H-NMR (DMSO-d$_6$)δ ppm: 0.96 (3H, d, J=6.7 Hz), 1.22 (3H, t, J=7.1 Hz), 2.15 (3H, s), 2.26 (3H, s), 2.9–3.3 (5H, m), 4.16 (2H, q, J=7.1 Hz), 4.76 (2H, s), 5.08 (1H, br m). 5.97 (1H, d, J=4.0 Hz), 6.68 (1H, s), 6.76 (2H, d, J=8.5Hz), 6.96 (1H, s), 7.17 (2H, d, J=8.5 Hz), 8.91 (2H, br s), 9.43 (1H, s)

Example 2

Crystalline form A of ethyl (−)-2-[4-[2-[[(1S,2R)-2-hydroxy-2-(4-hydroxyphenyl)-1-methyethyl]amino] ethyl]-2,5-dimethylphenoxy]acetate hydrochloride A mixture of 17.0 g of compound (I) obtained in Example 1 and ethanol (130 g) was heated at 70° C. with stirring until it appeared to be a clear solution. After insoluble materials were filtered off, the filtrate was cooled to 40° C., and seed crystals were added thereto. The mixture was stirred at 40° C. for 1.5 hours for crystallization, and t-butyl methyl ether (68 g) was added. After the resulting mixture was stirred for 1 hour additionally, the suspension was cooled to 20° C., and t-butyl methyl ether (58 g) was added. The suspension was allowed to stand overnight at room temperature, and then stirred for 3 hours under ice cooling. The precipitated crystals were collected by filtration, and dried at 60° C. overnight in vacuo to give 13.0 g of crystals. Melting point: 194–196° C.

The crystals were identified as crystalline form A by an X-ray powder diffraction analysis. An X-ray powder diffraction pattern was shown in FIG. 1.

Example 3

Crystalline form B of ethyl (−)-2-[4-[2-[[(1S,2R)-2-hydroxy-2-(4-hydroxyphenyl)-1-methyethyl]amino] ethyl]-2,5-dimethylphenoxy]acetate hydrochloride A mixture of 100 mg of compound (I) obtained in Example 1 and ethanol (245 μL) and tetrahydrofuran (45 μL) was heated at 75° C. with stirring until it appeared to be a clear solution. The solution was cooled to 40° C., and tetrahydrofuran (1.6 mL) was added. The resulting mixture was immediately cooled with ice bath, and stirring was continued for 7 hours. The mixture was allowed to stand overnight at room temperature, and then stirred for 2 hours under ice cooling. The precipitated crystals were collected by filtration, and dried at 60° C. overnight in vacuo to give 60.5 mg of crystals. Melting point: 177–179° C.

The crystals were identified as crystalline form B by an X-ray powder diffraction analysis. An X-ray powder diffraction pattern was shown in FIG. 2.

Stability Test

Stability test was carried out under a condition of storage at 60° C. for crystalline form A obtained in Example 2, crystalline form B obtained in Example 3 and the amorphous form of compound (II) obtained in Reference Example 1. The residual percentage of test substances was determined by HPLC, and the changes in appearance were observed.

TABLE 1

| Storage | Example 2 Crystalline form A | | Example 3 Crystalline form B | | Reference example 1 | |
|---|---|---|---|---|---|---|
| Period | Initial | 7 days | Initial | 7 days | Initial | 7 days |
| Residual percentage | 100 | 100 | 100 | 99.9 | 100 | 40.0 |
| Appearance | white | white | white | white | Colorless | tannish |

The results are shown in the above table 1. Crystalline forms A and B of the present invention indicate no changes in appearance and have excellent storage stabilities as compared with the amorphous compound (II).

INDUSTRIAL APPLICABILITY

The compound represented by formula (I) of the present invention has an excellent $\beta_3$-adrenoceptor stimulating effect and therapeutic effect on pollakiuria or urinary incontinence, and is useful as a medicament. The compound represented by formula (I) of the present invention has a highly crystalline property and can be obtained in high purity by a convenient purification procedure, and therefore is suitable for commercial production. Moreover, the particular crystalline forms A and B of the present invention have excellent storage stabilities, flowabilities and handling properties, and are suitable for formulation.

What is claimed is:

1. A crystalline compound represented by formula (I):

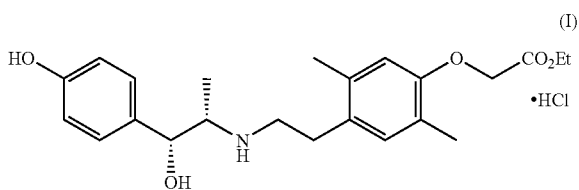

(I)

•HCl which shows an X-ray powder diffraction pattern having characteristic peaks at a diffraction antic (2θ±0.1 degree) of 8.9, 10.2, 12.9, 14.2, 15.6, 18.4 and 20.6 degrees.

2. A crystalline compound represented formula (I):

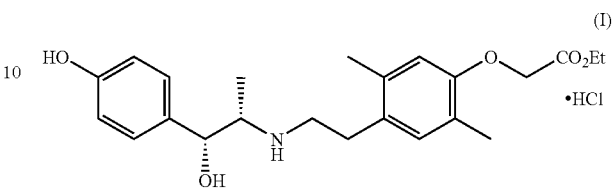

(I)

•HCl which shows an X-ray powder diffraction pattern having characteristic peaks at a diffraction angle (2θ±0.1 degree) of 7.3, 10.1, 12.2, 14.6, 15.9, 16.0, 18.7 and 21.8 degrees.

3. A pharmaceutical composition which comprises, as an active ingredient, a crystalline compound according to claim 1.

4. A pharmaceutical composition which comprises, as an active ingredient, a crystalline compound according to claim 2.

5. The pharmaceutical composition according to claim 3, for the treatment of pollakiuria or urinary incontinence.

6. The pharmaceutical composition according to claim 4, for the treatment of pollakiuria or urinary incontinence.

7. A medicament for treating pollakiuria or urinary incontinence, which comprises, as an active ingredient, a crystalline compound according to claim 1.

8. A medicament for treating pollakiuria or urinary incontinence, which comprises, as an active ingredient, a crystalline compound according to claim 2.

9. A method for treating pollakiuria or urinary incontinence, which comprises administering a therapeutically effective amount of a crystalline compound according to claim 1.

10. A method for treating pollakiuria or urinary incontinence, which comprises administering a therapeutically effective amount of a crystalline compound according to claim 2.

* * * * *